US008022181B2

(12) United States Patent
Srivastava

(10) Patent No.: US 8,022,181 B2
(45) Date of Patent: Sep. 20, 2011

(54) COMPOSITION AND METHOD FOR THE RELEASE OF PROTECTED PEPTIDES FROM A RESIN

(75) Inventor: Kripa Shanker Srivastava, Chesterfield, MO (US)

(73) Assignee: Mallinckrodt LLC, Hazelwood, MO (US)

(*) Notice: Subject to any disclaimer, the term of this patent is extended or adjusted under 35 U.S.C. 154(b) by 428 days.

(21) Appl. No.: 12/298,917

(22) PCT Filed: Apr. 18, 2007

(86) PCT No.: PCT/US2007/009475
§ 371 (c)(1),
(2), (4) Date: Oct. 29, 2008

(87) PCT Pub. No.: WO2007/130275
PCT Pub. Date: Nov. 15, 2007

(65) Prior Publication Data
US 2009/0221791 A1 Sep. 3, 2009

Related U.S. Application Data

(60) Provisional application No. 60/746,340, filed on May 3, 2006, provisional application No. 60/804,721, filed on Jun. 14, 2006.

(51) Int. Cl.
*C07K 1/04* (2006.01)
(52) U.S. Cl. .................. 530/333; 530/334; 530/338
(58) Field of Classification Search ................ None
See application file for complete search history.

(56) References Cited

U.S. PATENT DOCUMENTS

| | | | |
|---|---|---|---|
| 5,853,774 | A | 12/1998 | Dreve |
| 5,942,601 | A | 8/1999 | Miller et al. |
| 5,977,400 | A | 11/1999 | DeWitt et al. |
| 6,015,881 | A | 1/2000 | Kang et al. |
| 6,090,947 | A | 7/2000 | Dervan et al. |
| 6,281,331 | B1 | 8/2001 | Kang et al. |
| 6,566,520 | B2 | 5/2003 | DeWitt et al. |
| 6,683,189 | B1 | 1/2004 | Deryan et al. |
| 6,897,289 | B1 | 5/2005 | Obiols et al. |
| 6,946,562 | B2 | 9/2005 | Diehl et al. |
| 2002/0082384 | A1 | 6/2002 | Verdini et al. |
| 2004/0115774 | A1 | 6/2004 | Kochendoerfer et al. |
| 2005/0164912 | A1 | 7/2005 | Bigelow et al. |
| 2005/0165217 | A1 | 7/2005 | Guinn et al. |
| 2005/0287518 | A1 | 12/2005 | Hahn et al. |

FOREIGN PATENT DOCUMENTS

| | | |
|---|---|---|
| DE | 43 06 839 | 9/1994 |
| EP | 1 391 477 | 2/2004 |
| EP | 1 447 408 | 8/2004 |
| EP | 1 372 686 | 2/2005 |
| WO | WO 98/07752 | 2/1998 |
| WO | WO 98/17677 | 4/1998 |
| WO | WO 99/48513 | 9/1999 |
| WO | WO 2005/005457 | 1/2005 |
| WO | WO 2005/063791 | 7/2005 |
| WO | WO 2005/0637393 | 7/2005 |

OTHER PUBLICATIONS

Lloyd-Williams et al., "Solid-Phase Synthesis of Peptides Using Allylic Anchoring Groups. An Investigation of Their Palladium-Catalysed Cleavage", Tetrahedron Letters, 1991, vol. 32, No. 33, pp. 4207-4210, XP 002453560.
Barlos et al., "2-Chlorotrityl chloride resin", Int. J. Peptide Protein Res., 1991, vol. 37, pp. 513-520, XP 000206367.
Bollhagen et al., "A New Reagent for the Cleavage of Fully Protected Peptides synthesized on 2-Chlorotrityl Chloride Resin", J. Chem. Soc., Chem. Commun., 1994, pp. 2559-2250, XP 008084381.
Rink, "Solid-Phase Synthesis of Protected Peptide Fragments Using a Trialkoxy-Diphenyl-Methylester Resin.", Tetrahedron Letters, 1987, vol. 28, No. 33, pp. 3787-3790.
Mergler et al., "Peptide Synthesis by a Combination of Solid-Phase and Solution Methods I: A New Very Acid-Labile Anchor Group for the Solid Phase Synthesis of Fully Protected Fragments", Tetrahedron Letters, 1988, vol. 29, No. 32, pp. 4005-4008.
Barlos et al., "Darstellung Geschutzter Peptid-Fragmente Unter Einsatz Substituierter Triphenylmethyl-Harze", Tetrahedron Letters, 1989, vol. 30, No. 30, pp. 3943-3946.
Barlos et al., Veresterung Von Partiell Geschutzten Peptid-Fragmenten Mit Harzen. Einsatz Von 2-Chlortritylchlorid Zur Synthese Von Leu$^{15}$ —Gastrin I, Tetrahedron Letters, 1989, vol. 30, No. 30, pp. 3947-3950.
Barlos et al., "Synthesis of Prothymosin $x$ (ProT$x$)-a Protein Consisting of 109 Amino Acid Residues", Agnew. Chem. Int. Ed. Engl., 1991, 30, No. 5, pp. 590-593.
Stasiak et al., "Peptides derived from $x$-hydroxymethylserine: Aspects of solid-phase synthesis", Letters in Peptide Science 5: 1998, pp. 449-453.
Poulos et al., "Synthesis and biological activity of locust AKH-I and its analogues with modifications at the threonine residues", Int. J. Peptide Protein Res. 44, 1994, pp. 589-593.
Park et al., "Improved Loading and Cleavage Methods for Solid-Phase Synthesis Using Chlorotrityl Resins: Synthesis and Testing of a Library of 144 Discrete Chemicals as Potential Farnesyltransferase Inhibitors", J. Comb. Chem.., 2004, 6, pp. 407-413.
Nilsson et al., "Synthesis and Purification of Amyloidogenic Peptides", Analytical Biochemistry 288, 2001, pp. 76-82.
Aletras et al., "Preparation of the very acid-sensitive Fmoc-Lys(Mtt)-OH..", Int. J. Peptide Protein Res. 1994, 45, pp. 488-496.
Kamber et al., "The solid phase synthesis of protected peptides combined with fragment coupling in solution", Peptides, Chemistry and Biology, ESCOM, 1992, pp. 525-526.
Williams et al., "Convergent Solig-Phase Peptide Synthesis", 1993, Tetrahedron Letters 49: 11065-11133.
Andersson et al., "Large-Scale Synthesis of Peptides", 2000, Polymers 55: 227-250.
Poulow et al., Synthesis and biological activity of locust AKH-I and its analogues with modifications at the threonine residues, 1994, Int. J. Peptide Res., 44, pp. 589-593.

*Primary Examiner* — Christina Bradley

(57) ABSTRACT

The present invention provides a composition and a method for cleaving a peptide from a solid support resin. Hydrochloric acid in an organic water miscible solvent is used to cleave the peptide-resin attachment. Optionally, trifluoroethanol or hexafluoroisopropanol may be added to the cleavage composition to improve results. When using the present cleavage composition, an evaporation or other step to remove carboxylic byproducts is not necessary following the cleavage reaction. After the resin is filtered out of the cleavage mixture, the peptide may be immediately precipitated with water.

13 Claims, No Drawings

COMPOSITION AND METHOD FOR THE RELEASE OF PROTECTED PEPTIDES FROM A RESIN

CROSS REFERENCE TO RELATED APPLICATIONS

This application is a national stage application of PCT/US2007/009475, filed Apr. 18, 2007, which claims the benefit of U.S. Provisional Application No. 60/746,340 filed May 3, 2006 and of U.S. Provisional Application No. 60/804,721 filed Jun. 14, 2006.

BACKGROUND OF INVENTION

The present invention relates to peptide synthesis and, in particular, to solid phase peptide synthesis, or a combination of solid and liquid phase peptide synthesis. Many methods for peptide synthesis are described in the literature (for examples, see U.S. Pat. No. 6,015,881; Mergler et al. (1988) Tetrahedron Letters 29: 4005-4008; Mergler et al. (1988) Tetrahedron Letters 29: 4009-4012; Kamber et al. (eds), Peptides, Chemistry and Biology, ESCOM, Leiden (1992) 525-526; Riniker et al. (1993) Tetrahedron Letters 49: 11065-11133; and Andersson et al. (2000) Biopolymers 55: 227-250).

In solid phase peptide synthesis (SPPS), an amino acid or peptide group is bound to a solid support resin. Successive amino acids are attached to the support-bound peptide until the peptide of interest is formed. After the desired peptide is formed, it is cleaved from the resin. This requires cleaving the attachment between the peptide and resin and thereafter recovering the cleaved peptide using a suitable recovery technique.

Amino acids from which peptides are synthesized tend to have reactive side groups as well as reactive terminal ends. When synthesizing a peptide, it is important that the amine group on one peptide react with the carboxyl group on another peptide. Undesired reactions of side groups or at the wrong terminal end of a reactant produce unwanted by-products. To minimize side reactions, it is common practice to block reactive side groups and terminal ends of reactants to help make sure that the desired reaction occurs.

For example, a typical solid phase synthesis scheme involves attaching a first amino acid to the support resin via the carboxyl moiety of the first amino acid (although some synthesis schemes attach the first amino acid via the amine group). This allows the amine group of the resin bound amino acid to couple with an additional amino acid. Therefore, the carboxyl moiety of a new amino acid reacts with the free amine group of the resin bound material. To avoid side reactions involving the amine group of the new amino acid, the amine group is blocked with a protecting group during the coupling reaction. Two well-known amine protecting groups are the tert-butyloxycarbonyl (BOC) group and the 9-fluorenylmethyl carbamate (FMOC) group. Many others also have been described in the literature. After coupling, the protecting group (usually BOC or FMOC) on the N-terminus of the resin bound peptide can be removed, allowing additional amino acids to be added to the growing chain in a similar fashion. Reactive side chain groups of the amino acid reactants and the resin bound peptide can also be blocked with side chain protecting groups and remain blocked throughout the synthesis.

After synthesis, some or all of the side chain protecting groups can be removed from the peptide product. When substantially all of the protecting groups are removed, this is referred to as global deprotection. Global deprotection can occur contemporaneously with cleaving or can be carried out later if the peptide is to be further processed, modified, coupled to additional peptides or other material, etc. Some cleaving reagents not only cleave the peptide from the support resin, but also cause global deprotection to occur at the same time. For example, the strongly acidic cleaving reagents associated with BOC chemistry tend to cause global deprotection at the time of cleaving. Using the FMOC strategy, however, allows cleavage of the peptide from the resin while allowing the side chain protecting groups to remain so that further reactions, such as fragment condensation can, occur without substantial interference from side chain groups. Thus, the peptide is cleaved in a protected state.

Typically, the yield of a peptide synthesized by solid phase peptide synthesis decreases with increasing length of the peptide chain, i.e., the longer the peptide chain, the more likely undesirable side products will be produced along with the desired peptide. Therefore, for particularly long peptides, the final peptide product is produced in fragments, which are then combined later to form the desired peptide product. For example, a hypothetical 75 amino acid peptide may be synthesized in three peptide fragments, each fragment synthesized separately by solid-phase peptide synthesis. The fragments consisting of amino acids 1-25, amino acids 26-50, and amino acids 51-75 can be synthesized separately, then combined in fragment condensation steps to form the complete 75 amino acid final peptide product.

The prior art methods of cleaving a peptide from the resin support in a protected state typically create byproducts having carboxylic acids. Carboxylic acids will interfere with the subsequent fragment condensation reaction, creating unwanted byproducts. The prior art methods solved this problem by including an additional step following cleavage to remove the unwanted carboxylic acids, usually by evaporation of the cleavage solution. This extra step and the solvents needed cost additional time, expense, and create waste which must be disposed of, creating further expense. Therefore, there is a need for a method of cleaving a peptide from a resin more easily, cheaply, and efficiently by avoiding the production of unwanted carboxylic acid byproducts and, thereby, avoiding subsequent steps that remove the carboxylic acids.

SUMMARY OF INVENTION

The present invention provides a composition and a method for cleaving a peptide from a solid support resin. Hydrochloric acid in an organic water miscible solvent is used to cleave the peptide-resin attachment. Optionally, trifluoroethanol or hexafluoroisopropanol may be added to the cleavage composition to improve results. When using the present cleavage composition, an evaporation or other step to remove carboxylic byproducts is not necessary following the cleavage reaction. After the resin is filtered out of the cleavage mixture, the peptide may be immediately precipitated with water.

DETAILED DESCRIPTION

The present invention provides a composition and a method for cleaving a peptide from a solid support resin which dispenses with the need for a subsequent step to remove carboxylic acids from the cleavage mixture prior to condensation of peptide fragments, as is required when using prior art compositions and methods. The present invention can provide reduced processing time, increases in yield and purity, reduced amounts of reagents, starting materials, solvents, wastes, as well as other improvements relating to both small and large scale peptide synthesis. Peptides produced according to the present invention can be synthesized by methods well known in the art, and the present invention is not limited to any particular synthesis method. Any peptide may be produced according to the present invention.

An advantage of the FMOC synthesis strategy is that the synthesized peptide may be removed from the solid support resin in a substantially fully protected state, i.e., the side chain protecting groups remain on the peptide. This is due to the acid sensitive attachment of the peptide to the resin compared to the relatively strong attachment of the side chain protecting groups, which require a stronger acid in order to remove them from the peptide. Therefore, a relatively low concentration of acid may be used to cleave the peptide from the resin, while still allowing the side chain protecting groups to remain, as the acid solution is not strong enough to cleave these groups. Typically, a 2-chlorotrityl chloride resin is utilized to facilitate these advantages, as the attachment between the 2-chlorotrityl chloride resin and the peptide is relatively acid sensitive. However, other resins may be used. Although the present invention is described in connection with the FMOC peptide synthesis strategy, other solid phase peptide synthesis strategies and systems may be employed in combination with the present invention. The FMOC strategy is merely the preferred manner of synthesizing peptides on a large scale.

Typically, before the present invention, when the desired peptide is synthesized on a solid support resin, the peptide is removed from the resin using a solution of acetic acid (AcOH) or trifluoroacetic acid (TFA) in a solvent such as dichloromethane (DCM). However, using AcOH or TFA to cleave the peptide creates carboxylic acid byproducts in the cleavage mixture. If not removed, these carboxylic acids will interfere with subsequent reactions, such as fragment condensation reactions, where two or more peptide fragments are combined. Therefore, an additional step in the synthesis procedure is needed to remove the carboxylic acids. This is usually accomplished by evaporation of the cleavage mixture followed by reconstitution. This additional step requires more time, solvents, waste, expense, and can decrease yields and purity. Moreover, the carboxylic acids cannot be completely removed. Therefore, trace amounts will always be present, which can lower the purity of the final peptide product.

The present invention substantially eliminates the production of carboxylic acid byproducts and the costly and time consuming step of removing the carboxylic acids that is required in prior art methods by utilizing a novel cleavage reagent and method. In one embodiment, the cleavage reagent is a relatively low concentration of hydrochloric acid (HCl) in an organic water miscible solvent. Examples of organic water miscible solvents are dimethylformamide (DMF), N-methylpyrrolidone (NMP), dimethylacetamide (DMA), dimethyl sulfoxide (DMSO), tetrahydrofuran (THF), and dioxane. However, many other organic water miscible solvents are known in the art. A large range of concentrations of HCl will effectively cleave a peptide from the resin and all are within the scope of the present invention. However, the best results have been achieved in a particular range, preferably between about 0.05 N and about 0.5 N HCl, most preferably about 0.1 N HCl.

In another embodiment of the present invention, the inventive cleavage reagent further includes a fluorinated alcohol including but not limited to trifluoroethanol (TFE) or hexafluoroisopropanol (HFIP). The fluorinated alcohol is preferably in the range of about 1% to about 12%, more preferably about 5% to about 10%, and most preferably about 10% of the cleavage reagent. The inventors have found that from about 2 mL to 22 mL of reagent per gram resin, preferably from about 4 mL to 10 mL of reagent per gram resin, and more preferably from about 4 mL to 6 mL of reagent per gram resin is adequate to cleave the peptide from the resin. However, other amounts of the cleavage reagent will likely effectively cleave the peptide from the resin.

As discussed above, because substantially no carboxylic acid byproducts are produced when cleaving a peptide using the present cleavage reagent and method, an evaporation step to remove the carboxylic acid byproducts is not necessary. Therefore, several intermediate peptide fragments may be formed using the present invention and then combined in a fragment condensation step. One embodiment of the present invention is characterized by the absence of an evaporation step following cleavage. Following cleavage, the cleavage mixture may be filtered to remove the resin and optionally washed with solvent. The filtrate thus obtained is simply treated with water to precipitate the peptide fragment, which can then be filtered and optionally washed with water. Preferably cool water is used to precipitate the peptide, preferably in the temperature range of about 0° C. to about 25° C., most preferably about 0° C. However, warmer temperatures of water will also effectively precipitate the peptide from the cleavage filtrate. The inventors have found that at least about 4 mL of water per gram of the resin-peptide will effectively precipitate the cleaved peptide, although other amounts will likely work also.

Example

The following example briefly describes the synthesis of a peptide utilizing the present invention. Although the example describes the synthesis of enfuvirtide, the principles described can be applied to any peptide, preferably any protected peptide that is synthesized on an acid labile support such as chloro trityl chloride (CTC) resin, a Sieber resin, or a Rink resin. Non-limiting examples of such peptides include pramlintide, exenatide, enfuvirtide, calcitonin, and PYY-3-36. The following example is merely a preferred method of preparing enfuvirtide and is not meant to limit the present invention in any way.

Loading of FMOC-Amino Acid on CTC Resin:
1. General Method

A solution of FMOC amino acid (0.8 to 1.5 mole eq.) in DCM or DMF+DCM (4:1) containing DIEA (1 to 1.7 mole eq.) was added in the pres-swelled CTC resin (1 mole eq.) and was agitated for 2 hours under nitrogen current. It was drained and agitated with MeOH+DIEA (9:1) mixture for 20-30 minutes to destroy excess active chloride on the resin. The resin was filtered, washed with DMF (1×3 min.), DCM (1×3 min.), IPA (2×3 min.) and was dried to a constant weight. Substitution density of the loaded amino acid was determined by the weight gain method and the DBU analysis method.

2. Synthesis of Fragment-1: AC-AA (1-16)-CTR

The synthesis was performed manually in a 250 ml reactor starting with 17.5 g of FMOC-Gln-CTR (sub.=0.60 mm/g) and using FMOC-based SPPS. The FMOC-group was removed with 20% piperidine in NMP (2×20 min.) and coupling of all the FMOC-amino acids were performed by HBTU/HOBT method in presence of DIEA (1.5 eq. each) in NMP+DCM (3:1) except for FMOC-Gln (Trt) at position 15, which was done using 2.5 mole equivalents of the reagents. All the amino acids were incorporated by a single coupling except Asn (trt)14, Gln (trt)13 and Ser (tBu)12 where double coupling was required. After the removal of FMOC group of the last amino acid, the resin was treated with 5 mole equivalents of acetic anhydride and pyridine in NMP for an hour to incorporate the acetyl group at the N-terminus. The yield of the fully protected peptide-resin was 34.9 g (72.8%) compared to a theory yield of 48 g. According to HPLC, the purity of the peptide was >89.1% (at 262 nm).

3. Synthesis of Fragment-2: FMOC-AA(17-26)-CTR

The synthesis was started with 25 g of FMOC-Leu-CTR (sub.=0.8 mm/g) using HBTU/HOBT (1.5 mole eq.) coupling method. All the amino acids (1.5 mole eq.) were incorporated by a single coupling using NMP+DCM (3:1) as a coupling solvent and DIEA (1.5 mole eq.) as a base. The completeness of the coupling was monitored by the Kaiser test. The removal of the FMOC group was accomplished with 20% piperidine in DMC (2×20 min.). The yield of the protected peptidyl resin was 58.7 g (93.4%) compared to a theory yield of 62.9 g. According to HPLC, the purity of the peptide was >97.1% (at 262 nm).

4. Synthesis of Fragment-3: FMOC-AA(27-35)-CTR

The synthesis was started with 37.5 g of FMOC-Trp (BOC)-CTR (sub.=0.7 mm/g) using HBTU/HOBT coupling method in NMP+DCM (3:1) as a solvent. All the amino acids were coupled by a single coupling except the last amino acid FMOC-Asp (otBu) which was coupled twice (2×2 hours) followed by acetylation. 1.5 fold excess of amino acids and reagents were used for the coupling and the completion of the coupling was monitored by the Kaiser method. The yield of the peptide resin was 73 g (89.3%) compared to a theory yield of 81.8 g. According to HPLC, the purity of the peptide was >80.65% (at 220 nm).

5. Cleavage of the Protected Fragments from the Support a. Cleavage of Fragment-1: Ac-AA(1-16)-OH 10.0 g (2 mm) of Ac-AA(1-16)-CTR was stirred with 100 ml of 0.1 N HCl in DMF for 4.5 hours at room temperature and was filtered followed by washing with DMF. The combined filtrate was added to 0° C. stirred water and precipitated solid was filtered followed by washing with water and dried to yield 5.62 g (78.5%) of the protected peptide, compared to a theory yield of 7.2 g. According to HPLC, the purity was >85.64% (IPA system). When the peptide resin was cleaved with 0.1 N HCl in DMF containing 10% TFE, the yield of the protected peptide was 92% with an HPLC purity >96.86% (IPA system).

b. Cleavage of Fragment-2: FMOC-AA(17-26)-OH

A sample of protected peptide resin (5 g, 1.7 mm) was agitated with 50 ml of 0.1 N HCl in DMF for 4.5 hours and was filtered followed by washing with DMF. The filtrate was added to a 0° C. stirred water and the precipitated solid was filtered, washed with water and dried to yield 2.9 g (74.2%) of the protected peptide. According to HPLC, the purity of the peptide was >90.1% (ACN system) and >81% (IPA system). When the cleavage of the peptide resin was performed with 0.1 N HCl in DMF containing 10% TFE, the yield of the peptide was 91.6% and HPLC purity was >96.66% (IPA system).

c. Cleavage of Fragment-3: FMOC-AA(27-35)-OH

A 2.5 g (0.8 mm) sample of peptidyl resin was stirred with 25 ml of 0.1 N HCl in DMF including 10% TFE at room temperature for 4.5 hours and was filtered. The filtrate was added to a 0° C. stirred water and the solid obtained was collected by filtration followed by washing with water. After drying for overnight it yielded 72.4% (1.28 g) of the desired peptide with an HPLC purity of 84%. When the cleavage of the peptide resin was done with 0.1 N HCl in DMF containing 5% TFE, the yield of the protected peptide was 67.9 g (1.2 g) and the purity was 88.2%.

6. Synthesis of Protected Enfuvirtide by Fragment Condensation in Solution a. Coupling of Fragment-3 with Phe-NH2 into FMOC-AA(27-36)-NH2

A mixture of fragment-3 (2.62 g, 1 eq.), Phe-NH2 (0.24 g, 1.2 eq.) and HOAT (0.2 g, 1.2 eq.) was stirred with 30 ml. of DMF in presence of DIEA (0.43 ml; 2.1 eq.) and the solution was treated with HBTU (0.55 g, 1.2 eq.) at 0° C. for 15-20 minutes and then at room temperature for 70-80 minutes. The progress of the reaction was monitored by TLC (CM-10) and HPLC. The reaction mixture was cooled at 0° C. and was treated with 20-30 ml of water and colorless solid separated out was filtered followed by washing with water and dried to yield 2.76 g (98.6%) of FMOC-AA(27-36)-NH2. According to HPLC, the purity of the peptide was >88.15%. The experiment was repeated several times and the yields obtained ranged from 97 to 100% with a purity between 82.6 to 88.2%.

b. Deprotection of FMOC-AA(27-36)-NH2 into H-AA(27-36)-NH2 Fragment-4

A solution of FMOC-AA(27-36)-NH2 (1.16 g, 0.5 mm) in 5 ml of 5% piperidine in DMA was stirred for 2 hours at room temperature and was then diluted with 15 ml of water at 0° C. with stirring. The colorless solid separated was filtered followed by washing with water and dried. It was washed with ether and hexane (one time each) to yield 0.91 g (86.7%) of the product with an HPLC purity of 85.85% (ACN system).

c. Coupling of Fragment-2 and 4 into F-AA(17-36)-NH2

[A] HBTU/HOAT Method

A solution of fragment-2 (1.80 g, 0.8 mm, 1 eq.), fragment-4 (1.68 g=0.8 mm), HBTU (0.3 g, 0.8 mm), and HOAT (0.16 g, 1.2 mm, 1.5 eq.) in 23 ml DMF containing DIEA (0.2 ml, 1.2 mm) was stirred at 0-5° for 15-20 minutes and at room temperature for 2 hours and the progress of the reaction was monitored by TLC in CMA (90:8:2) and HPLC. It was treated with 23 ml of cold water at 0-5° C. and after stirring for 30 minutes it was filtered followed by washing with water and dried to yield 3.53 g (101.2%) of the product with a purity of 79.4%. After crystallization with 95% IPA/H20, the yield was 74.5% and the purity was 89.96%. It was contaminated with trace amounts of fragment-2 (0.24%) and fragment-4 (0.15%) (IPA system).

[B] TBTU/HOAT Method

The coupling reaction was performed in DMA solvent using TBTU in the same molar proportion as mentioned above and the yield was 3.56 g (101.95%) with a purity of 70.2%. After crystallization with 95% IPA/H20, the yield was 74.5% (2.6 g) with an HPLC purity of 88.4% (IPA system).

It was deblocked with piperidine (10 eq.) in DMA and was isolated with water to yield 93.3% of the product with ah HPLC purity of 85.3% (IPA system).

d. Coupling of Fragment-1 with H-AA(17-36)-NH2 into Protected Enfuvirtide.

Stirred fragment-1 (0.4 g, 1 eq.), HOAT (0.03 g, 1.5 eq.) and DIEA (0.03 ml, 1.5 eq.) in 8 ml DMA to get a clear solution and then stirred it at 0.5° C. Added TBTU (0.04 g, 1 eq.) and stirred the solution at 0° C. for 15-20 minutes and then added a solution of H-AA(17-36)-NH2 (0.5 g, 1 eq.) in DMA and continued stirring at 0° C. for 30 minutes and then at room temperature for 2 hours. Added cold water (~15 ml) at 0° C. and filtered separated solid followed by washing with water and dried to yield protected enfuvirtide in 97.3% (0.9 g) yield with ah HPLC purity of >66.93% (IPA system). After crystallization with 95% ACN/H20, the yield was 55.3% and the purity of the peptide was >72.8%. (scheme-1)

7. In-situ Coupling of the Fragments a. Release of F-AA(27-35)-OH from its CTC Resin 5.0 g (1.62 mm) of FMOC-M(27-35)-CTR was stirred with 25 ml of 0.1 N HCl in DMF for 4 hours and was filtered followed by washing once with 10 ml of DMF. Total volume of FMOC-AA(26-35)-OH in DMF=35 ml (1.62 mm, assumed).

b. Preparation of FMOC-AA(27-36)-NH2→H.AA(27-36)-NH2

The above solution (from step #1) was stirred at 0° C. and was neutralized with DIEA to pH~7. A 1.2 fold excess of Phe-NH2 (0.32 g, 1.94 mm), HOAT (0.26 g), HBTU (0.74 g) and 2.1 fold excess of DIEA (0.6 ml, 3.4 mm) were added and the mixture was stirred at 0° C. for 0.5 hours and at room temperature for 2 hours. The completion of the reaction was monitored by TLC (CM-10). Now, DBU (10 eq.) was added and stirring was continued for another 2 hours and progress of the deblocking was monitored by TLC (CM-10) and HPLC.

c. Release of FMOC-AA(17-26) from the Support and its Coupling with H-AA(27-36)-NH2 into FMOC-AA(17-36)-NH2→H.AA(17-36)-NH2

4.7 g (1.62 mm) of FMOC-AA(17-26)-CTR was stirred with 25 ml of 0.1 N HCl in DMF for 4 hours, filtered followed by washing with 10 ml of DMF (total volume=35) and the solution was stirred at 0° C. It was treated with a solution of H-AA(27-36)-NH2 (step #2) and the pH of the mixture was adjusted to 7. HOAT, HBTU (1 mole eq. each) and the DIEA (1.8 mole eq.) were added and the mixture was stirred at 0° C. for 0.5 hours and at room temperature for 2 hours to overnight. The progress of the reaction was monitored by TLC (CM-10) and HPLC. The mixture was now treated with DBU (10 eq.) for 2 hours to remove the N-terminal FMOC group (mixture volume=70 ml). It was neutralized to pH~7 at 0° C. for use in the next reaction.

d. Release of Ac-AA(1-16)-OH from the Support and its Coupling with H-AA(17-36)-NH2 into AC-AA(1-36)-NH2

8.3 g (1.62 mm) of AC-AA(1-16)-CTR was cleaved with 40 ml of 0.1 N HCl in DMF for 4 hours as described above and the filtered solution pH was adjusted to 7 at 0° C. It was then treated with HOAT (1.5 eq), DIEA (1.5 eq.) and HBTU (1 eq.) in order and after stirring at 0° C. for 15-20 minutes, the deblocked solution (step #3) was added and stirring was continued for 0.5 hours at 0° C. and for 2 hours to overnight at room temperature. It was now added to a stirred water (~300 ml) while solid precipitated out. After stirring for an hour, the solid was filtered followed by washing with water and dried. The dried solid was washed with hexane to yield 10.9 g (91.2%) of the product. According to HPLC, the product purity was only 32.71% and contained approximately 26% of the unreacted fragment-1.

It was therefore, reacted again using 50% amount of the H-AA(17-36)-NH2, HOAT, DIEA and HBTU and was worked up as usual to yield 13.2 g (110%) of the product. According to HPLC, the peptide purity was 45.7%.

When 0° C. stirred solution of isolated fragment-1 (0.98 g, 0.3 mm) in DMF was condensed with a DBU de-FMOCked and neutralized solution of isolated FMOC-AA (17-36)-NH2 (1.31 g, 0.3 mm) in DMF in presence of 1.5 mole equivalent of HOAT, DIEA and 1 mole equivalent of HBTU, the isolated yield of the product was 91.9% (2 g) with an HPLC purity of >62.1%.

In a similar manner, when isolated H-(17-36)-NH2 was coupled with unisolated fragment-1, the yield and purity of the peptide was 95.7% and 33.6%, respectively.

The invention claimed is:

1. A method of peptide synthesis comprising:
   a. cleaving a resin bound intermediate peptide fragment from a resin by subjecting the resin-peptide attachment to a composition comprising:
      an organic water miscible solvent,
      from 0.05 N to 0.5 N hydrochloric acid, and
      from about 1% to about 12% of a fluorinated alcohol, thus creating a cleavage mixture comprising a non-resin bound intermediate peptide fragment;
   b. precipitating said intermediate peptide fragment by treating said cleavage mixture with water; and
   c. combining at least two intermediate peptide fragments generated from steps a and b and performing a fragment condensation reaction with said at least two intermediate peptide fragments;
   wherein said method does not include an evaporation step in between steps a-c, and wherein said cleaving step a produces substantially no carboxylic acid byproducts.

2. The method of claim 1, wherein the concentration of hydrochloric acid is 0.1 N.

3. The method of claim 1, wherein the fluorinated alcohol is trifluoroethanol or hexafluoroisopropanol.

4. The method of claim 3, wherein the composition comprises from 5% to 10% trifluoroethanol.

5. The method of claim 3, wherein the composition comprises about 10% trifluoroethanol.

6. The method of claim 3, wherein the composition comprises from about 5% to about 10% hexafluoroisopropanol.

7. The method of claim 3, wherein the composition comprises about 10% hexafluoroisopropanol.

8. The method of claim 3, wherein the organic water miscible solvent is dimethylformamide, N-methylpyrrolidone, dimethylacetamide, dimethyl sulfoxide, tetrahydrofuran, or dioxane.

9. The method of claim 8, wherein the organic water miscible solvent is dimethylformamide.

10. The method of claim 3, wherein during cleaving the resin-peptide is subjected to about 2 mL to about 22 mL of composition per gram resin-peptide.

11. The method of claim 3, wherein during cleaving the resin-peptide is subjected to about 4 mL to about 10 mL of composition per gram resin-peptide.

12. The method of claim 3, wherein during cleaving the resin-peptide is subjected to about 4 mL to about 6 mL of composition per gram resin-peptide.

13. The method of claim 3, wherein during precipitating the intermediate peptide fragment, the cleavage mixture is treated with at least about 4 mL of water per gram of resin-peptide.

* * * * *